United States Patent
Fahrig et al.

(10) Patent No.: US 11,464,469 B2
(45) Date of Patent: Oct. 11, 2022

(54) MEDICAL IMAGING SYSTEM COMPRISING A MAGNET UNIT AND A RADIATION UNIT

(71) Applicant: Siemens Healthcare GmbH, Erlangen (DE)

(72) Inventors: Rebecca Fahrig, Mohrendorf (DE); Martino Leghissa, Wiesenthau (DE); Simon James Calvert, Finstock (GB); Adrian Mark Thomas, Bicester (GB)

(73) Assignee: Siemens Healthcare GmbH, Erlangen (DE)

( * ) Notice: Subject to any disclaimer, the term of this patent is extended or adjusted under 35 U.S.C. 154(b) by 439 days.

(21) Appl. No.: 16/461,159

(22) PCT Filed: Apr. 25, 2017

(86) PCT No.: PCT/EP2017/059690
§ 371 (c)(1),
(2) Date: May 15, 2019

(87) PCT Pub. No.: WO2018/095587
PCT Pub. Date: May 31, 2018

(65) Prior Publication Data
US 2019/0274649 A1    Sep. 12, 2019

(30) Foreign Application Priority Data

Nov. 23, 2016    (EP) .................................. 16200280.2

(51) Int. Cl.
*G01R 33/48*    (2006.01)
*A61B 6/00*    (2006.01)
(Continued)

(52) U.S. Cl.
CPC .......... *A61B 6/4417* (2013.01); *A61B 5/0035* (2013.01); *A61B 5/055* (2013.01);
(Continued)

(58) Field of Classification Search
CPC ............ G01R 33/4808; G01R 33/4812; A61N 2005/1055; A61B 6/4417
See application file for complete search history.

(56) References Cited

U.S. PATENT DOCUMENTS

| 5,713,357 A | 2/1998 | Meulenbrugge et al. |
| 8,788,016 B2 | 7/2014 | Roell et al. |
| (Continued) | | |

FOREIGN PATENT DOCUMENTS

| CN | 103260700 A | 8/2013 |
| CN | 103608692 A | 2/2014 |
| (Continued) | | |

OTHER PUBLICATIONS

Japanese Office Action and English translation thereof dated Sep. 1, 2020.
(Continued)

*Primary Examiner* — James M Kish
(74) *Attorney, Agent, or Firm* — Harness, Dickey & Pierce, P.L.C.

(57) ABSTRACT

A medical imaging system a magnet unit includes a main magnet and a first housing. In an embodiment, the main magnet is arranged inside the first housing and includes coil elements and at least one coil carrier, the magnet unit defining an examination opening. The first radiation unit is embodied to irradiate the examination object and is arranged on the side of the magnet unit. The magnet unit includes a first region, transparent to radiation emitted by the first radiation unit radially to the examination axis. The first radiation unit is embodied to emit radiation through the first region of the magnet unit in a direction of the examination opening and is furthermore embodied to rotate about the examination opening.

19 Claims, 10 Drawing Sheets

(51) Int. Cl.
| | |
|---|---|
| *A61B 5/00* | (2006.01) |
| *A61B 5/055* | (2006.01) |
| *G01R 33/38* | (2006.01) |
| *G01R 33/3815* | (2006.01) |
| *A61N 5/10* | (2006.01) |

(52) U.S. Cl.
CPC .......... *A61B 6/4014* (2013.01); *A61B 6/4064* (2013.01); *A61B 6/4435* (2013.01); *A61B 6/5247* (2013.01); *G01R 33/3804* (2013.01); *G01R 33/3815* (2013.01); *G01R 33/4812* (2013.01); *A61B 6/4258* (2013.01); *A61N 5/1049* (2013.01); *A61N 2005/1054* (2013.01); *A61N 2005/1055* (2013.01); *G01R 33/4808* (2013.01)

(56) References Cited

U.S. PATENT DOCUMENTS

| | | | |
|---|---|---|---|
| 2003/0181808 A1 | 9/2003 | McKinnon | |
| 2006/0236709 A1 | 10/2006 | Steinmeyer | |
| 2008/0208036 A1 | 8/2008 | Amies et al. | |
| 2009/0149735 A1 | 6/2009 | Fallone et al. | |
| 2011/0012593 A1 | 1/2011 | Demeester | |
| 2011/0196227 A1* | 8/2011 | Gross | G01R 33/4812 600/411 |
| 2011/0199085 A1* | 8/2011 | Allen | A61N 5/1049 324/309 |
| 2013/0261430 A1* | 10/2013 | Uhlemann | A61B 5/0036 600/411 |
| 2013/0345546 A1 | 12/2013 | Hobeika | |
| 2014/0107468 A1* | 4/2014 | Calvert | A61N 5/1039 600/411 |
| 2014/0136615 A1 | 5/2014 | Kruip | |
| 2015/0173699 A1 | 6/2015 | Kyriakou | |
| 2015/0247907 A1* | 9/2015 | Heid | A61B 6/4417 600/411 |
| 2016/0114191 A1* | 4/2016 | Sankey | A61N 5/1071 378/65 |
| 2016/0256712 A1 | 9/2016 | Vahala et al. | |
| 2016/0291104 A1 | 10/2016 | Tsuda | |
| 2017/0135599 A1 | 5/2017 | Brown | |
| 2018/0325477 A1* | 11/2018 | Wang | A61B 5/0035 |

FOREIGN PATENT DOCUMENTS

| | | | | |
|---|---|---|---|---|
| CN | 103800009 A | 5/2014 | | |
| CN | 105536153 A | 5/2016 | | |
| CN | 105658278 A | 6/2016 | | |
| CN | 105873509 A | 8/2016 | | |
| DE | 102004061869 B4 | 8/2008 | | |
| GB | 2393373 A | * | 9/2002 | ............ G01R 33/48 |
| GB | 2393373 A | | 3/2004 | |
| GB | 2527538 A | | 12/2015 | |
| GB | 2531730 A | | 5/2016 | |
| WO | WO 2012164527 A1 | | 12/2012 | |
| WO | WO 2014/044314 A1 | * | 3/2014 | ........ G01R 33/4812 |
| WO | WO 2014044314 A1 | | 3/2014 | |
| WO | WO 2015079921 A1 | | 6/2015 | |
| WO | WO 2015181939 A1 | | 12/2015 | |

OTHER PUBLICATIONS

Lagendijk, Jan J. W. et al. "MRI/linac integration" Radiotherapy and Oncology vol. 86,pp. 25-29, 2008.

Wang, Ge et al. "Vision 20/20: Simultaneous CT-MRI—Next chapter of multimodality imaging" Medical Physics, vol. 42, No. 10, pp. 5879-5889, 2015 // ISSN: 0094-2405, DOI: 10.1118/1.4929559.

Lagendijk, Jan J.W. et al. "MR guidance in radiotherapy" Physics in Medicine & Biology, vol. 59, pp. R349-R369, 2014 // DOI: 10.1088/0031-9155/59/21/R349.

Fahrig, Rebecca et al. "A Truly Hybrid Interventional MR/X-Ray System: Feasibility Demonstration" Journal of Magnetic Resonance Imaging, vol. 13, pp. 294-300, 2001 // https://doi.org/10.1002/1522-2586(200102)13:2<294::AID-JMRI1042>3.0.CO;2-X.

Ganguly, Arundhuti et al. "Truly Hybrid X-Ray/MR Imaging: Toward a Streamlined Clinical System" Academic Radiology, No. 12, pp. 1167-1177, 2005 // DOI: 10.1016/j.acra.2005.03.076.

International Search Report and Written Opinion dated August 1.2017.

Extended European Search Report dated Jun. 2, 2017.

Chinese Office Action and English translation thereof dated Apr. 2, 2021.

European Office Action dated Jun. 11, 2021.

Chinese Office Action and English translation thereof dated Nov. 2, 20201.

Japanese Notice of Allowance dated Dec. 15, 2020.

CA Chinese Office Action and English translation thereof dated Jun. 23, 2021.

* cited by examiner

MEDICAL IMAGING SYSTEM COMPRISING A MAGNET UNIT AND A RADIATION UNIT

PRIORITY STATEMENT

This application is the national phase under 35 U.S.C. § 371 of PCT International Application No. PCT/EP2017/059690 which has an International filing date of Apr. 25, 2017 and which claims priority to European Application No. EP 16200280.2 filed Nov. 23, 2016, the entire contents of each of which are hereby incorporated herein by reference.

The activity leading to this application has received funding from the European Institute of Innovation and Technology (EIT) under grant agreement No EIT/EIT HEALTH/SGA2017/1. This European body receives support from the European Union's Horizon 2020 research and innovation programme.

FIELD

An embodiment of the present application is directed to a medical imaging system including a magnet unit and a radiation unit.

BACKGROUND

Magnetic resonance imaging (MRI) is an imaging method characterized by particularly high soft-tissue contrast. Therefore, it can in particular be used in the diagnosis of tumors and in angiography.

In such fields of application, it is furthermore known to use radiation units such as X-ray sources or particle radiation sources. In this case, particle radiation can in particular be electron radiation or Hadron radiation. These radiation units can, on the one hand, be used together with a suitable detector for imaging and, on the other, for the manipulation of tissue.

In numerous medical diagnostic applications, it is desirable to use both MR image data and image data obtained from radiation units. During the manipulation of tissue by way of particle radiation, it is furthermore desirable to monitor the position and other characteristics of the irradiated tissue via MR imaging.

It is known to perform MR imaging and irradiation at different times of via an MR device and via a radiation device separate from the MR device. In this case, however, the patient has to be transported between the two different devices or even relocated. Furthermore, because of the time between the two procedures, it is possible that the anatomy of the patient can change, for example due to respiration or metabolic processes. This complicates the combination of MR imaging with irradiation.

It is known from US 2015/0247907 A1 to operate an X-ray source and an X-ray detector in the examination opening of magnetic resonance scanner. However, this requires both the X-ray source and the X-ray detector to be designed to be operated in strong magnetic fields.

It is furthermore known from the publication GANGULY, Arundhuti et al.: "Truly Hybrid X-Ray/MR Imaging: Toward a Streamlined Clinical System", in: Academic Radiology (12) 2005, pages 1167-1177, to use an MR device comprising a plurality of magnet units and to embody the radiation unit such that beam path passes through the different magnet units. Although this does not cause the radiation unit to be influenced by the strong magnetic field in the examination opening of the MR device, the plurality of magnet units makes it difficult to achieve a homogeneous magnetic field necessary for the MR imaging in the examination opening.

SUMMARY

At least one embodiment of the present invention provides an efficient possibility for simultaneous MR imaging and the exposure of the examination object to radiation.

At least one embodiment of the present invention is directed to a medical imaging system. Advantageous embodiments are described in the claims.

At least one embodiment of the present invention relates to a medical imaging system, comprising a magnet unit embodied for magnetic resonance imaging of an examination object and a first radiation unit embodied to irradiate the examination object, wherein the magnet unit comprises a main magnet and a first housing, wherein the main magnet is arranged inside the first housing and wherein the main magnet comprises coil elements and at least one coil carrier. The magnet unit furthermore defines an examination opening along an examination axis such that the magnet unit surrounds the examination opening. The magnet unit furthermore comprises a first region that is transparent to radiation emitted by the first radiation unit radially to the examination axis. The first radiation unit is furthermore arranged on the side of the magnet unit facing away from the examination opening and embodied to emit radiation through the first region of the magnet unit in the direction of the examination opening. The first radiation unit is furthermore embodied to rotate about the examination opening.

BRIEF DESCRIPTION OF THE DRAWINGS

The following describes and explains the invention in more detail with reference to the example embodiments shown in the figures, in which.

DETAILED DESCRIPTION OF THE EXAMPLE EMBODIMENTS

Figure 1:
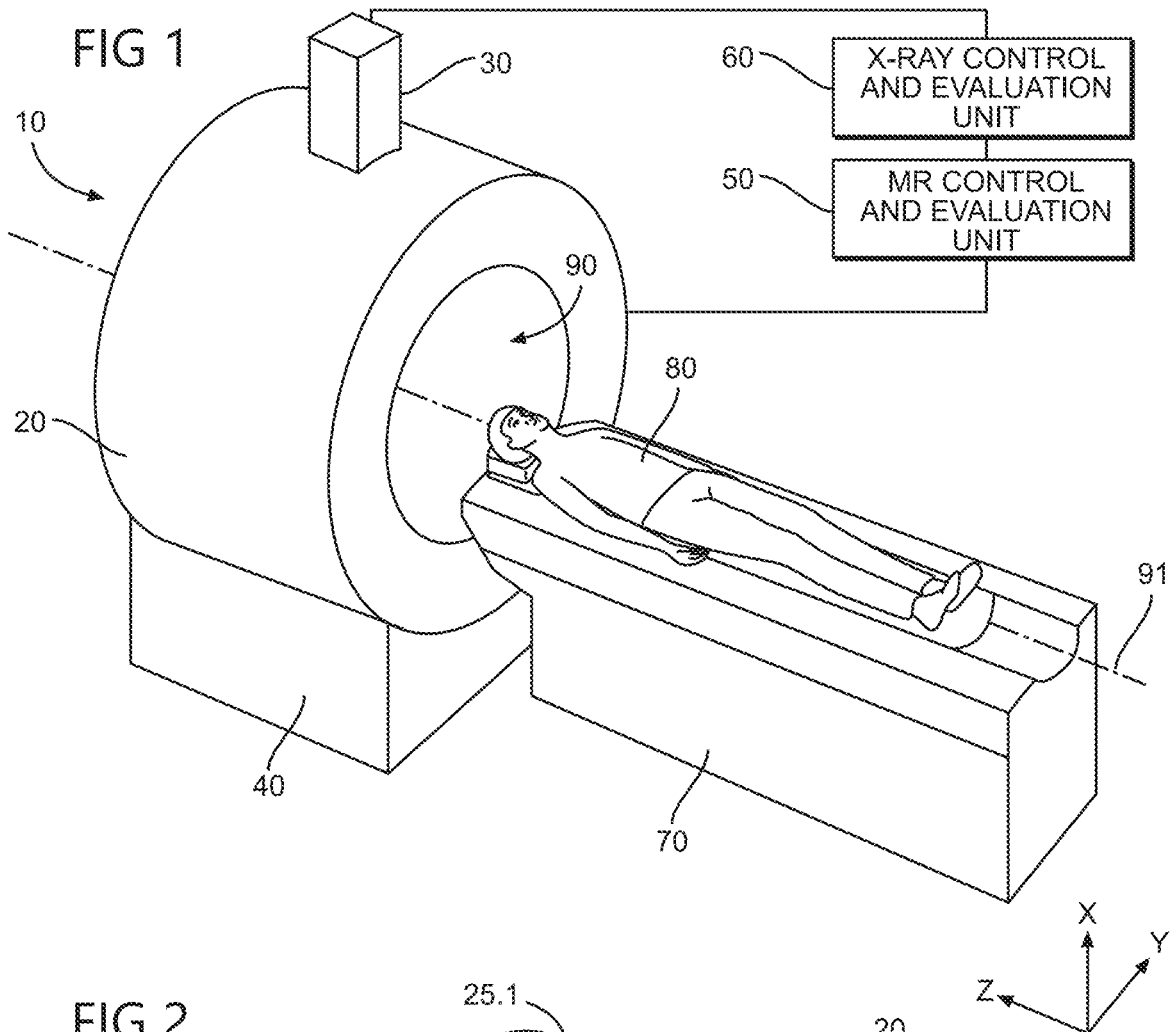
FIG. 1 shows a perspective view of a medical imaging system.

At least one embodiment of the present invention relates to a medical imaging system, comprising a magnet unit embodied for magnetic resonance imaging of an examination object and a first radiation unit embodied to irradiate the examination object, wherein the magnet unit comprises a main magnet and a first housing, wherein the main magnet is arranged inside the first housing and wherein the main magnet comprises coil elements and at least one coil carrier. The magnet unit furthermore defines an examination opening along an examination axis such that the magnet unit surrounds the examination opening. The magnet unit furthermore comprises a first region that is transparent to radiation emitted by the first radiation unit radially to the examination axis. The first radiation unit is furthermore arranged on the side of the magnet unit facing away from the examination opening and embodied to emit radiation through the first region of the magnet unit in the direction of the examination opening. The first radiation unit is furthermore embodied to rotate about the examination opening.

The first region of the magnet unit is, in particular in an embodiment, transparent to radiation from the first radiation unit such that the intensity of radiation from the first radiation unit emitted radially to the examination axis and passing through the first region is attenuated to a lesser degree than the intensity of radiation from the first radiation unit emitted radially to the examination axis which does not pass through the first region.

In particular in an embodiment, the attenuation of the intensity of the radiation passing through the first region after passing through the magnet unit is less than half or less than 10% or less than 1% of the attenuation of the intensity of the radiation that does not pass through the first region after passing through the magnet unit. The examination opening is in particular embodied to receive the examination object. The first radiation unit can in particular be embodied outside the magnet unit. The medical imaging system can in particular comprise precisely one magnet unit. The inventors have recognized that the arrangement of the radiation unit outside the magnet unit does not cause this to be influenced by the strong main magnetic field in the examination opening during the MR imaging. It is, therefore, possible to use inexpensive radiation units that are not designed to be operated in strong magnetic fields.

A further advantage of an arrangement of the first radiation unit outside the magnet unit, of at least one embodiment, compared to the arrangement in the examination opening, is that that more space is available for the first radiation unit outside the magnet unit and therefore it is possible to use more efficient and/or stronger first radiation units. The inventors have furthermore recognized that an arrangement outside the magnetic fields also makes the first radiation unit very easily accessible for maintenance work.

The inventors have furthermore recognized that the region of the magnet unit transparent to the radiation from the first radiation unit means it is not necessary to use a plurality of separate magnet units. This enables a more homogeneous magnetic field and hence more accurate MR imaging to be achieved than with a plurality of separate magnet units in at least one embodiment.

According to a further possible embodiment of the invention, the magnet unit furthermore comprises a first outlet region that is transparent to radiation from the first radiation unit emitted radially to the examination axis through the first region and the examination object and wherein the first outlet region does not overlap the first region. The inventors have recognized that an additional first outlet region on the one hand enables a radiation detector also to be arranged outside the magnet unit. A first outlet region can furthermore be used to divert the non-diffuse radiation from the first radiation unit out of the magnet unit without interacting with and damaging the magnet unit.

According to a further embodiment of the invention, the coil elements of the main magnet and the at least one coil carrier are arranged outside the first region of the magnet unit. In particular there is no coil element of the main magnet and no coil carrier arranged within the first region of the magnet unit. The inventors have recognized that this geometry of the coil elements and of the coil carrier of the main magnet can enable transparency to the radiation from the radiation unit to be achieved particularly efficiently and inexpensively since no special materials have to be used for the coil elements of the main magnet and for the at least one coil carrier and there is no radiation intensity loss on the transillumination of the coil elements of the main magnet or the at least one coil carrier.

According to a further embodiment of the invention, in the first region, the magnet unit comprises at least one internal window and at least one external window in the first housing, wherein the internal window and the external window are transparent to the radiation emitted by the first radiation unit radiation. In this case, the internal window is arranged on the side of the magnet unit facing the examination opening, in particular as part of the first housing. In this case, the external window is furthermore arranged on the side of the magnet unit facing away from the examination opening, in particular as part of the first housing. The inventors have recognized that the use of at least two windows enables the structure and hence the stability of the magnet unit to be maintained and simultaneously transparency of the first region of the magnet unit to be achieved.

The internal window and the external window are in particular transparent in that the material of the internal and the external window is more transparent to the radiation from the first radiation unit than the material of the first housing. In particular, the attenuation of the intensity of radiation on passage through the window is less than half or less than 10% or less than 1% of the attenuation of the intensity on passage through the first housing.

According to a further possible embodiment of the invention, the interior window and/or the exterior window are made of beryllium. The inventors have recognized that windows made of beryllium can be produced cost-efficiently. In addition, such windows will be less susceptible to radiation damage than windows made of other materials with smaller mass number of the atomic nucleus such as graphite.

According to a further embodiment of the invention, the first region is embodied as a funnel in the magnet unit extending radially to the examination axis and which can be penetrated by the radiation emitted by the first radiation unit radially to the examination axis. A funnel is in particular a continuous opening in the magnet unit. The inventors have recognized that the use of a funnel causes the radiation sent from the radiation unit through the magnet to be only very weakly attenuated.

According to a further embodiment of the invention, the funnel can in particular be formed by the first housing of the magnet unit; in particular the side walls of the funnel can be formed by the first housing. The inventors have recognized that the formation of the funnel by the first housing enables the magnet unit to be embodied as particularly stable, and in particular an enclosed cooling system to be embodied as simply and inexpensively as possible.

According to a further embodiment of the invention, the funnel can in particular be filled with a material transparent to the radiation from the first radiation unit. The inventors have recognized that filling with a radiolucent material enables the stability of the magnet unit to be increased.

According to a further possible embodiment of the invention, the medical imaging system furthermore comprises a first radiation detector, wherein the first radiation detector is embodied to detect radiation sent from the first radiation unit through the first region of the magnet unit and wherein the first radiation detector is arranged on the side of the examination object facing away from the first radiation unit. A first radiation detector can in particular be a first X-ray detector, a gamma detector and/or a particle detector. The inventors have recognized that the detection of the radiation can be used to measure the radiation dose to which the examination object is exposed due to irradiation with the radiation from the first radiation unit and hence to minimize the radiation dose.

According to a further embodiment of the invention, the first radiation unit is a particle source embodied to generate particle radiation. The inventors have recognized that irradiation by way of particle radiation enables a particularly large amount of energy to be deposited in a tissue and that the irradiation is therefore particularly effective.

According to a further embodiment of the invention, the first radiation unit is a radioactive source embodied to generate particle radiation or gamma radiation. The inventors have recognized that a radioactive source is not influenced by a magnetic field outside of the magnet unit, so the radioactive source does not have to be shielded or modified. Using such a radioactive source is therefor particularly cheap.

According to a further possible embodiment of the invention, the particle source is embodied to generate electron and/or Hadron radiation. The inventors have recognized that electron and/or Hadron radiation can be generated particularly simply and inexpensively with a particle radiation source.

According to a further embodiment of the invention, the first radiation unit is a first X-ray source. The medical imaging system furthermore comprises a first X-ray detector, wherein the first X-ray detector is arranged on the side of the examination object facing away from the first X-ray source and wherein the first X-ray source and the first X-ray detector are embodied for X-ray imaging of the examination object. The inventors have recognized that X-rays emitted by a first X-ray source and received via a first X-ray detector enable imaging that is efficiently supplemented by the MR imaging because the MR imaging has good soft-tissue contrast and the X-ray imaging is an efficient way of depicting bone structures and contrast media.

The inventors have furthermore recognized that an arrangement of the first X-ray source outside the magnet unit results in a greater distance and a smaller enlargement ratio for the X-ray projections than an arrangement in the examination opening. This reduces the radiation dose absorbed by the surface of the examination object, in particular the skin of a patient, and the blurring of the X-ray projections.

According to a further embodiment of the invention, the first X-ray detector can be arranged in the main magnetic field of the main magnet. The inventors have recognized that a first X-ray detector is, on the one hand, much more insensitive to high magnetic fields than a first X-ray source and that, on the other, due to the arrangement in the main magnetic field, the X-rays only have to pass the main magnet once and not a second time, which is linked to an attenuation of intensity. Therefore, this arrangement also does not require an outlet region of the magnet unit to be transparent to X-rays.

According to a further embodiment of the invention, the first X-ray detector can be curved. The inventors have recognized that, with a curved embodiment, more space is left in the examination opening for examination objects and/or it is possible to use a larger first X-ray detector.

According to a further embodiment of the invention, the magnet unit can comprise a first outlet region and furthermore the first X-ray detector is arranged outside the magnet unit on the side of the magnet unit facing away from the examination opening before the first outlet region such that the first X-ray detector can receive X-rays emitted by the first X-ray source through the first region. The inventors have recognized that the arrangement of the first X-ray detector outside the magnet unit enables the examination opening to be embodied at large as possible.

According to a further embodiment of the invention, the first X-ray detector is embodied to rotate about the examination opening simultaneously with the first X-ray source. The inventors have recognized that simultaneous rotation causes the relative position between the first X-ray source and the first X-ray detector to remain constant and the X-ray imaging does not have to be adapted to a changed relative position. The simultaneous rotation furthermore makes it possible, instead of a large, non-rotatable first X-ray detector, to use a first X-ray detector that is as small as possible and hence inexpensive.

According to a further embodiment of the invention, the magnet unit is embodied to rotate about the examination opening. The inventors have recognized that this enables the first region of the magnet unit to be rotated in different alignments and irradiation from different directions can always pass through only one transparent region of the magnet unit. This means that the transparent region of the magnet unit only has to be as large as the beam path of the radiation unit. A first region that is small as possible increases the stability of the magnet unit; furthermore the coil elements of the main magnet and the coil carrier of the main magnet can be arranged in a larger volume, which simplifies the generation of a homogeneous magnetic field. A first region that is as small as possible furthermore simplifies the arrangement of a gradient coil unit and a radio-frequency antenna unit outside the first region and hence improves the quality of the gradient field and the radio-frequency field.

According to a further embodiment of the invention, the magnet unit comprises a gradient coil unit, wherein the orientation of the gradient coil unit is fixed relatively to the examination opening, and wherein the main magnet is embodied to rotate about the examination opening. In other words, the orientation of the gradient coil unit is variable with respect to the main magnet. The magnet unit can also comprise a radio-frequency antenna which is fixed relatively to the examination opening. In other words, the orientation of both the gradient coil unit and the radio-frequency antenna can be variable with respect to the main magnet. In particular, the orientation of the radio-frequency antenna is fixed relatively to the gradient coil unit. The inventors have recognized that within such a configuration conventional pulse sequences can be used for the gradient coil unit and/or the high frequency antenna, due to the relative position of the gradient coil unit and the examination volumes being fixed, which is simpler and cheaper than using adapted pulse sequences for the gradient coil unit and/or the high frequency antenna.

According to another possible embodiment of the invention, the medical imaging system comprises a second housing, wherein the second housing comprises the gradient coil unit, and wherein the second housing is transparent to radiation emitted by the first radiation unit radially to the examination axis; furthermore, the medical imaging system comprises means for rotating the first housing relatively to the second housing. The inventors have recognized that in this arrangement the relative position of the gradient coil unit and the main magnet can be changed very easily.

According to a further embodiment of the invention, the first radiation unit and the main magnet are embodied to rotate simultaneously about the examination opening. In particular, the first radiation unit can be connected to the magnet unit. In particular, the first radiation unit can be connected to the magnet unit such that the radiation emitted by the first radiation unit passes through the first transparent region of the magnet unit. The inventors have recognized that simultaneous rotation of the first radiation unit with the magnet unit means that no separate, time-intensive alignment and/or positioning of the first radiation unit is necessary during the examination. Furthermore, the first region of the magnet unit can be selected as small as possible. The inventors have furthermore recognized that, in this arrangement, the magnetic field of the main magnet unit outside the examination opening that penetrates the first radiation unit does not depend upon the orientation of the first radiation unit. This enables measures to compensate the magnetic field to be taken in the first radiation unit which are not dependent upon the orientation of the first radiation unit.

According to a further embodiment of the invention, the magnet unit is designed to cool the coil elements of the main magnet by way of heat conduction. The inventors have recognized that cooling by way of heat conduction is less expensive than convection-based cooling by way of immersion in a coolant because cooling by way of heat conduction requires less coolant. The inventors have furthermore recognized that, with cooling by way of heat conduction, the cooling efficiency is not influenced, or is only influenced less than with cooling by way of immersion, by the alignment of the magnet unit. This enables efficient cooling even in the case of a magnet unit that is designed to rotate.

According to a further embodiment of the invention, the waste heat from the coil elements of the main magnet is dissipated by pipes containing a circulating coolant. The inventors have recognized that the pipes enable particularly effective cooling. The inventors have furthermore recognized that the first region can be embodied as particularly transparent to the radiation from the first radiation unit when the pipes are arranged outside the first region of the magnet unit.

According to a further embodiment of the invention, the coil elements of the main magnet are made of an electrically superconducting material, wherein the critical temperature of the superconducting material is higher than the boiling point of helium. The inventors have recognized that a critical temperature higher than the boiling point of liquid helium enables the use of coolants other than liquid helium and/or cooling methods other than immersion in liquid helium, in particular cooling by way of heat conduction. Therefore, this type of cooling is less expensive and furthermore particularly advantageous with a magnet unit embodied to rotate; furthermore this type of cooling is particularly advantageous for embodying the first region of the magnet unit transparent to the radiation from the first radiation unit.

According to a further possible embodiment of the invention, the electrically conductive material of the coil elements of the main magnet is magnesium diboride. The inventors have recognized that magnesium diboride is a metallic superconductor with a particularly high critical temperature. This enables the use of measures for cooling the coil elements, which are particularly inexpensive and transparent to the radiation emitted by the radiation unit.

According to a further embodiment of the invention, the medical imaging system furthermore comprises a second radiation unit, wherein the second radiation unit is arranged on the side of the magnet unit facing away from the examination opening. The magnet unit furthermore comprises a second region that is transparent to radiation emitted by the second radiation unit radially to the examination axis. The second radiation unit is furthermore embodied to emit radiation through the second region of the magnet unit in the direction of the examination opening; the second radiation unit is furthermore embodied to rotate about the examination opening. In particular, the second radiation unit can be arranged outside the magnet unit. The inventors have recognized that a second radiation unit based on MR imaging and X-ray imaging that is present in addition to a first X-ray source enables irradiation to be performed via the first X-ray source with the second radiation unit. This enables the use of the complementary image information from the MR imaging and the first X-ray imaging. This enables the second radiation unit to be used particularly efficiently.

The second region of the magnet unit is in particular transparent to radiation from the second radiation unit such that the intensity of radiation from the second radiation unit emitted radially to the examination axis and passing through the second region is attenuated to a lesser degree than the intensity of radiation from the second radiation unit emitted radially to the examination axis which does not pass through the first region or through the second region. In particular, the attenuation of the intensity of the radiation passing through the second region during said passage is less than half or less than 10% or less than 1% of the attenuation of the intensity of the radiation that does not pass through the first and or the second region.

According to a further embodiment of the invention, the second radiation unit is a second X-ray source; the medical imaging system radiation furthermore comprises a second X-ray detector, wherein the second X-ray detector is arranged on the side of the examination object facing away from the second X-ray source. The second X-ray detector is furthermore embodied to rotate about the examination opening simultaneously with the second X-ray source. The second X-ray source and the second X-ray detector are furthermore embodied for X-ray imaging of the examination object. The inventors have recognized that such an arrangement enables two X-ray projections to be recorded simultaneously from two different directions without having to rotate the X-ray sources or to rotate the magnet unit. This enables the reconstruction of a three-dimensional X-ray image data set without rotation of the X-ray sources or rotation of the magnet unit.

According to a further possible embodiment of the invention, the magnet unit furthermore comprises a second outlet region that is transparent to radiation emitted from the first radiation unit radially to the examination axis through the second region and the examination object, wherein the second outlet region does not overlap with the second region. The inventors have recognized that an additional second outlet region on the one hand enables a radiation detector also to be arranged outside the magnet unit. A second outlet region can furthermore be used to divert the non-diffuse radiation from the second radiation unit out of the magnet unit without interacting with and damaging the magnet unit.

According to a further embodiment of the invention, the second X-ray detector can comprise further features of the first X-ray detector. All advantages assigned to one embodiment of the first X-ray detector can also be assigned to the corresponding embodiment of the second X-ray detector.

According to a further embodiment of the invention, the second region of the magnet unit, the first outlet region and/or the second outlet region can comprise all further features of the first region of the magnet unit. All advantages assigned to one embodiment of the first region of the magnet unit can also be assigned to the corresponding embodiments of the second region, the first outlet region and/or the second outlet region.

According to a further embodiment of the invention, the connecting line from the first X-ray source and the first X-ray detector and the connecting line from the second X-ray source and the second X-ray detector enclose an angle of between 60 and 120 degrees or between 80 and 100 degrees or between 85 and 95 degrees. The inventors have recognized that the angle between the connecting lines corresponds to the angle between the projection directions of the X-ray projections recorded with the two X-ray sources and the two X-ray detectors. An angle of this kind between the X-ray projections enables three-dimensional X-ray projections to be reconstructed from the two-dimensional X-ray projections in a particularly efficient way.

In an embodiment, a magnet unit can in particular be cylinder-shaped, ring-shaped and/or torus-shaped. The magnet unit furthermore comprises a side facing the examination opening, which is called the internal side; the magnet unit furthermore comprises a side facing away from the examination opening, which is called the external side. The magnet unit surrounds the examination opening such that it surrounds the examination opening along a loop around the preferential direction; therefore, the examination opening is in particular open at two ends. The magnet unit also surrounds an examination opening if it has design-related recesses.

In an embodiment, a radiation unit emits electromagnetic radiation or particle radiation. Electromagnetic radiation can in particular be X-rays or gamma rays. X-rays in particular designate electromagnetic radiation with a wavelength of between 1 pm and 500 pm, in particular between 5 pm and 250 pm, in particular between 5 pm and 60 pm. Gamma in particular designates electromagnetic radiation with a wavelength of less than 5 pm, in particular less than 1 pm, regardless of the generation of the radiation. The spectra of X-rays and gamma radiation can be monochromatic or polychromatic. Particle radiation in particular corresponds to a stream of particles in a common direction. Particles can, in particular, be leptons or baryons. Baryons can in particular be protons or neutrons. Leptons can in particular be electrons, positrons or muons.

A first region, a second region and/or an outlet region of the magnet unit are in particular transparent to the radiation from the first radiation unit when the intensity of the radiation after passing through the first region, the second region and/or the outlet region is at least 10%, in particular at least 50%, in particular at least 90%, in particular at least 95%, in particular at least 99%, in particular at least 99, 9% of the intensity of the radiation before passing through the first region, the second region and/or the outlet region. The magnet unit is in particular more transparent to radiation from the first radiation unit emitted radially to the examination axis and passing through the first region, the second region and/or the outlet region than for radiation from the first radiation unit emitted radially to the examination axis which does not pass through the first region, the second region and/or the outlet region, if the attenuation of the intensity of the radiation emitted radially to the examination axis which does not pass through the first region, the second region and/or the outlet region is greater than the attenuation of the intensity of the radiation emitted radially to the examination axis which passes through the first region, the second region and/or the outlet region by more than a factor of 2, in particular by more than a factor of 5, in particular by more than a factor of 10, in particular by more than a factor of 50. In this case, the intensity designates the energy of the radiation per unit area and per time unit. In the case of monochromatic electromagnetic radiation, the intensity of the radiation is in particular proportional to the quadratic amplitude of the variable electrical field. In the case of particle radiation, the intensity of the radiation is in particular proportional to the energy of the particles and to the number of particles per time unit.

A first unit and a second unit in particular rotate simultaneously about an axis or a region when they rotate about or the region with the same angular velocity. Therefore, the angle between the first connecting line of the first unit and the axis or the region and the second connecting line of the second unit and the axis or the region also in particular remains constant.

The cooling of coil elements of a magnet can take place by heat conduction, heat convection and/or heat radiation. The coil elements of the main magnet of an MR device are embodied, for example, for cooling by way of heat convection in that they are stored in liquid helium. The coil elements of the main magnet of an MR device can furthermore be embodied for cooling by way of heat conduction.

Superconductor designates materials with an electrical resistance that falls to zero when a critical temperature is fallen below (another technical term is transition temperature). Superconducting materials are in particular used in coils and coil elements for the generation of strong magnetic fields.

A first unit, which is arranged on the side of a third unit facing away from a second unit does not have to be part of third unit or comprised by the third unit. A first unit is in this case in particular, viewed from the third unit, arranged behind the second unit, however, the first unit can in particular also be attached or arranged directly on the second unit. A first unit, which is arranged on the side of a third unit facing a second unit does have to be part of the third unit or comprised by the third unit. A first unit is in this case in particular, viewed from the third unit, arranged before the second unit, the first unit can in particular also be attached or arranged directly on the second unit.

FIG. 1 is a perspective view of a medical imaging system 10. In this example embodiment, the medical imaging system 10 comprises a magnet unit 20, a first X-ray source 30, a support and rotating appliance 40, an MR-control and evaluation unit 50, an X-ray-control and evaluation unit 60 and a support appliance 70 on which an examination object 80 is located. The magnet unit 20 comprises an examination opening 90 embodied to receive the patient support appliance 70 with the patient 80.

In this example embodiment, the magnet unit 20 is embodied in the shape of a hollow cylinder around an examination axis 91, wherein the examination axis 91 extends parallel to a third coordinate axis z. Also depicted are a first coordinate axis x and a second coordinate axis y, which together with the third coordinate axis z form a three-dimensional Cartesian coordinate system.

In this example embodiment, the magnet unit 20 is embodied by way of the support and rotating appliance 40 rotatably about the examination opening 90, in particular rotatably about the examination axis 91. At the same time, the first X-ray source 30 is permanently connected to the magnet unit 20 so that, on a rotation of the magnet unit 20 about the examination axis 91, the first X-ray source 30 is also rotated about the examination axis 91 and about the examination opening 90.

The magnet unit 20 is connected to the MR-control and evaluation unit 50. The first radiation unit 30 is connected to the radiation-control and evaluation unit 60. The MR-control and evaluation unit 50 is furthermore connected to the radiation-control and evaluation unit 60, in particular the MR-control and evaluation unit 50 and the radiation-control and evaluation unit 60 are able to exchange image information and/or control signals with one another. It is also alternatively possible for the MR-control and evaluation unit 50 and the radiation-control and evaluation unit 60 to be implemented in a common control and evaluation unit.

In the example embodiment shown, the examination object 80 is a patient 80, and the support appliance 70 a patient support appliance 70. The patient support appliance 70 is embodied to transport the patient 80 into the cylindrical examination opening 90.

Figure 2:
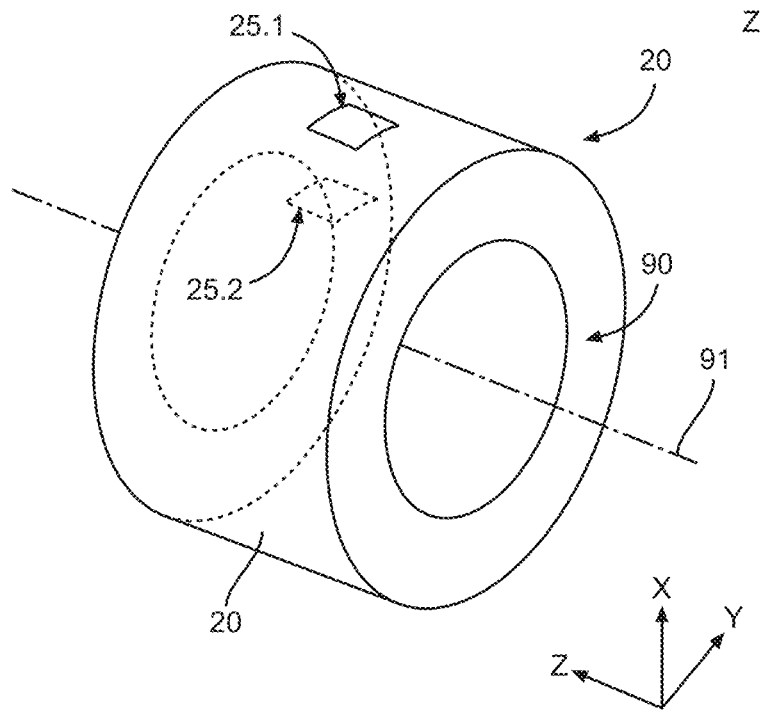
FIG. 2 shows a magnet unit with an internal and an external window.

FIG. 2 shows a magnet unit 20 with an external window 25.1 and an internal window 25.2, wherein the windows are embodied as part of the first housing 26 of the magnet unit 20. In this example embodiment, the first region of the magnet unit 20 is bounded by the external window 25.1 and the internal window 25.2. Here, the external window 25.1 and the internal window 25.2 are made of glass. However, the two windows 25.1, 25.2 can also be made of beryllium, aluminum or another material, wherein the other material is transparent to the radiation 32 from the first radiation unit 30. In the example embodiment shown, the external window 25.1 and the internal window 25.2 are rectangular. However, the two windows 25.1, 25.2 can also be round, oval or have another shape. The design of the external window 25.1 and the internal window 25.2 can in particular take account of the necessary stability of the magnet unit 20 and the geometric shape of the beam path of the radiation 32 from the first radiation unit 30.

In the example embodiment shown in FIG. 2, the magnet unit 20 is embodied to rotate about the examination axis 91 and only precisely one first region of the magnet unit 20 is bounded by the external window 25.1 and the internal window 25.2. If the magnet unit 20 is embodied not to rotate about the examination axis 91, it is alternatively possible to use a magnet unit 20 with a plurality of first regions and hence a plurality of external windows 25.1 and internal windows 25.2 or a magnet unit 20 with a larger first region defined by a larger external window 25.1 and by a larger internal window 25.2 so that the first radiation unit 30 can irradiate the examination object 80 from different directions. In the example embodiment, the external window 25.1 and the internal window 25.2 are adapted in an arched shape to the curvature of the first housing 26 of the magnet unit 20. It is also possible to use a flat external window 25.1 and/or a flat internal window 25.2.

Figure 3:
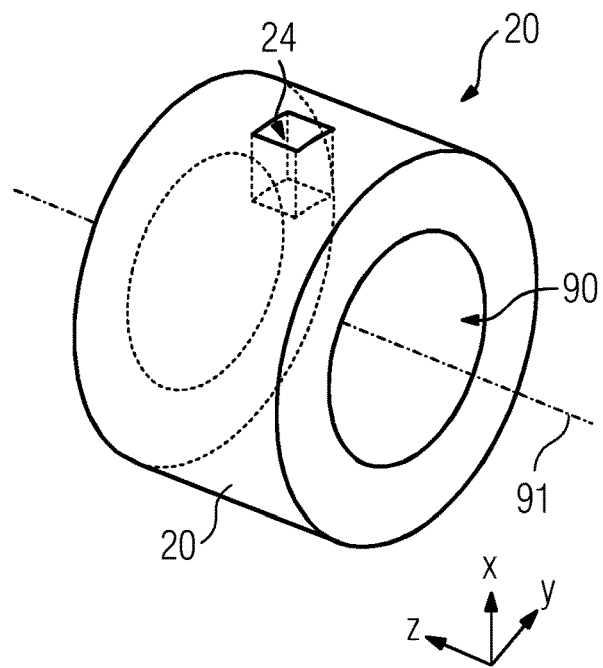
FIG. 3 shows a magnet unit with a funnel.

FIG. 3 shows a magnet unit 20 forming a funnel 24 as a first region. The funnel 24 is in particular formed by the first housing 26 of the magnet unit 20. In this example embodiment, the funnel 24 is embodied in a prism shape with a rectangular base. However, the funnel 24 can also be embodied in a prism shape with a base of a different shape or as a pyramid frustum or cone frustum. In particular, it is possible for the funnel 24 to be cylindrical. The design of the funnel 24 can in particular take account of the necessary stability of the magnet unit 20 and the geometric shape of the beam path of the radiation 32 from the first radiation unit 30. In the example embodiment, the funnel 24 is filled with air. However it is also possible to fill the funnel 24 with another material which can be penetrated by the radiation emitted by the first radiation unit 30. If the first radiation unit 30 is a first X-ray source 30, the funnel 24 can in particular also be filled with Plexiglas.

In the example embodiment shown in FIG. 3, the magnet unit 20 is embodied to rotate about the examination axis 91 and only precisely one first region of the magnet unit 20 is formed by a funnel 24. If the magnet unit 20 is embodied not to rotate about the examination axis 91, it is alternatively possible to use a magnet unit 20 with a plurality of first regions and hence a plurality of funnels 24 or a magnet unit 20 with a larger first region with a larger funnel 24 so that the first radiation unit 30 can irradiate the examination object 80 from different directions.

Figure 4:
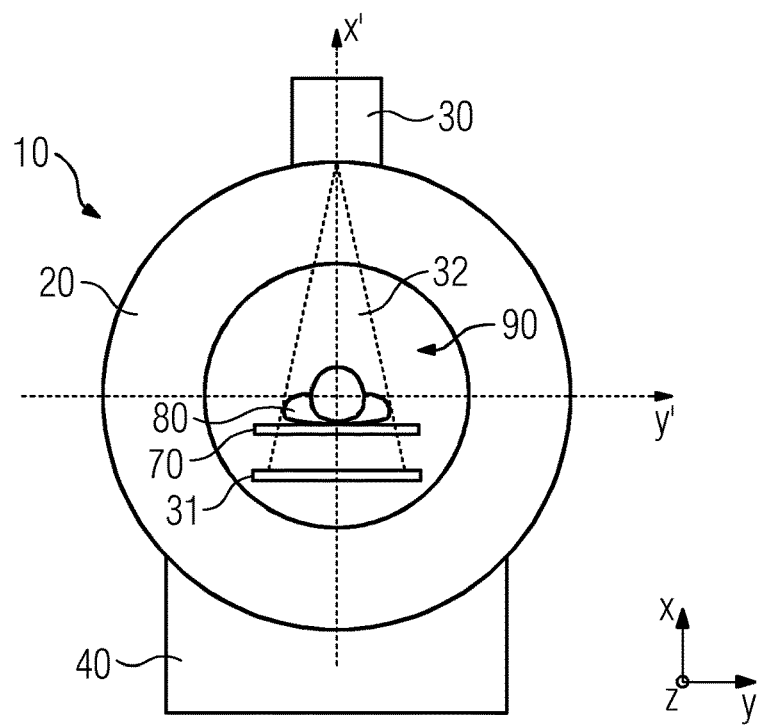
FIG. 4 shows a section through the medical imaging system perpendicular to the examination axis.
Figure 5:
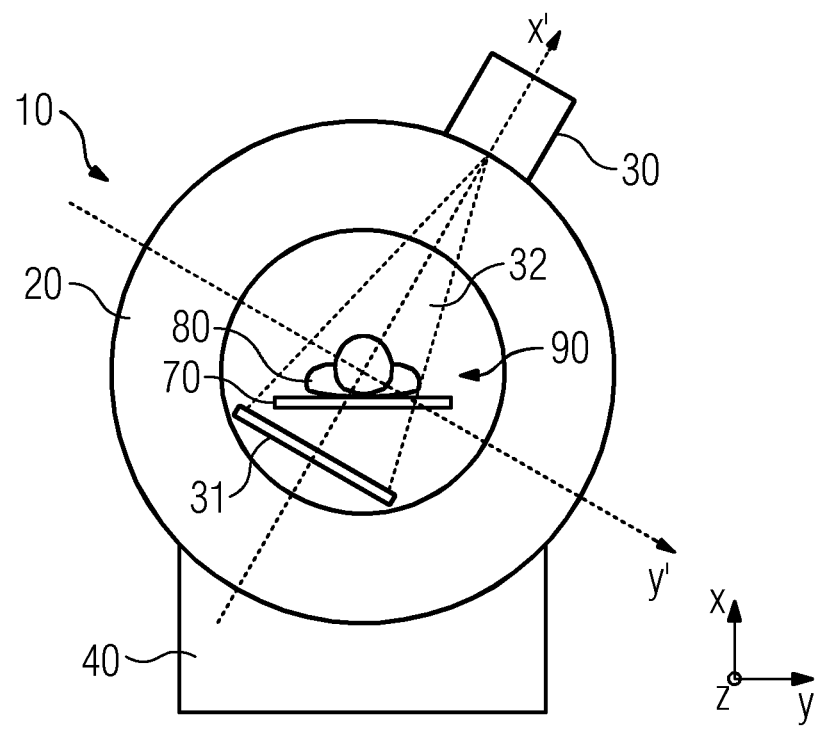
FIG. 5 shows a section through the medical imaging system perpendicular to the examination axis, wherein the magnet unit has been rotated.

FIG. 4 shows a section through the medical imaging system 10 orthogonal to the examination axis 91, in particular a section through the magnet unit 20. FIG. 5 also shows a section through the medical imaging system 10 orthogonal to the examination axis 91, in particular a section through the magnet unit 20. In the example embodiment shown, the magnet unit 20 is embodied to rotate; the first radiation unit 30 is furthermore permanently connected to the magnet unit 20 and embodied to rotate jointly and simultaneously with the magnet unit 20 about the examination opening 90. The orientation of the magnet unit 20 is specified by a first rotated coordinate axis x' and a second rotated coordinate axis y', wherein the second rotated coordinate axis y' is orthogonal to the first rotated coordinate axis x' and wherein the first rotated coordinate axis x' and the second rotated coordinate axis y' are orthogonal to the examination axis 91 and hence to the third coordinate axis z. In the example embodiment shown, the first radiation unit 30 corresponds to a first X-ray source and the medical imaging system 10 furthermore comprises a first X-ray detector 31. It is obviously also possible for the magnet unit 20 to be connected to another first radiation unit 30 and embodied to rotate simultaneously about the examination axis 91. In the example embodiment shown in FIG. 4 and FIG. 5, the first X-ray detector 31 is embodied to rotate simultaneously with the first X-ray source 30 and hence simultaneously with the magnet unit 20. Alternatively, the first X-ray detector 31 could also be embodied as stationary; in this case, it is necessary to use a much larger and/or a curved first X-ray detector 31 in order to detect the X-rays 32 from the first X-ray source 30 from different directions.

In the example embodiment shown, the first radiation unit 30 is a first X-ray source 30 embodied to emit X-rays 32. However, the first radiation unit 30 can also be embodied to emit gamma radiation or particle radiation. The first radiation unit 30 can also be a radioactive source, in particular a Cobalt-60 source emitting gamma radiation. The usage of a radioactive source has the advantage that the radioactive source is not influenced by a strong magnetic field.

In the example embodiment shown, the first X-ray source 30 is embodied as a first X-ray tube 30 with a rotating anode. A first X-ray tube 30 can in particular be embodied together with a first X-ray detector 31 for the X-ray imaging of the examination object 80 in that X-ray projections of the examination object 80 are recorded. In this case, a first X-ray tube with rotating anode and a first X-ray detector 31 are known from the prior art. The use of a plurality of X-ray projections of an examination object with respect to different projection directions can also enable the reconstruction of a three-dimensional X-ray image data set.

A first X-ray source 30 can alternatively also be embodied as a first X-ray tube with a static anode or a liquid metal jet anode. A first X-ray source can furthermore be embodied as a linear accelerator or LINAC. Compared to an X-ray tube, a linear accelerator is in particular able to generate X-rays with a shorter wavelength. These X-rays can then in particular be used for the manipulation of a region of the examination object 80. In this case, it is in particular possible for the irradiation to destroy tissue, in particular tumor tissue. A linear accelerator can also generate particle radiation.

A linear accelerator comprises a linear acceleration unit embodied along an axis. The linear acceleration unit can be embodied parallel to the first rotated coordinate axis x'. The linear acceleration unit can also be embodied in another direction, in particular parallel to the third coordinate axis z or parallel to the second rotated coordinate axis y'. In this case, the space requirements above the magnet unit 20 is particularly small and the medical imaging system 10 can be used in standard examination chambers, although then an additional deflection unit has to be used in the case of particle radiation in order to emit the radiation 32 through the first region of the magnet unit 20 correctly.

A first X-ray detector 31 can, as shown in the example embodiment depicted, be embodied as flat. In this case, different embodiments are known for a flat X-ray detector 31, for example made of amorphous silicon or complementary metal-oxide semiconductors (commonly abbreviated to "CMOS"). Also known are photon-counting first X-ray detectors and first X-ray detectors comprising a screen-film, wherein the screen-film converts X-rays 32 into visible light. The first X-ray detector 31 can alternatively also be curved or curved in parts.

As shown in the example embodiment in FIG. 4 and FIG. 5, the first X-ray detector 31 can be embodied within the examination opening 90. The X-ray detector can furthermore also be embodied between the main magnet 21 and the examination opening 90, in particular between the parts or within the gradient coil unit 22 or the parts or within the radio-frequency antenna unit 23. However, alternatively, the first X-ray detector 31 can also be arranged outside the magnet unit 20 on the side of the magnet unit 20 facing away from the first X-ray source. In this case, the magnet unit 20 comprises an outlet region 27 transparent to the radiation 32 from the first radiation unit 30, wherein, after passing through the examination object 80, the radiation 32 passes through the outlet region 27.

Figure 6:
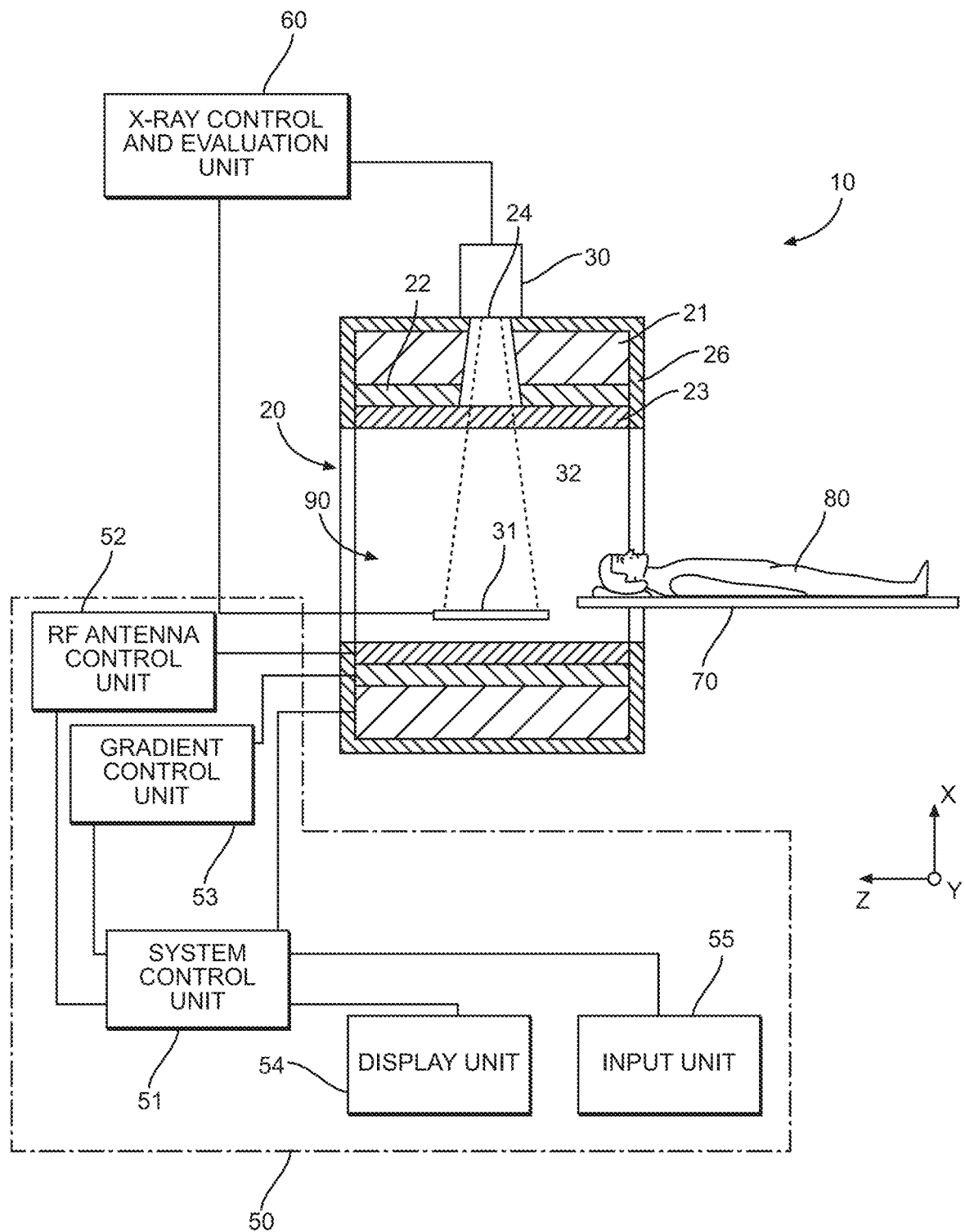
FIG. 6 shows a section through the medical imaging system parallel to the examination axis.

FIG. 6 is a schematic depiction of the mode of operation of a magnet unit 20 with reference to a section orthogonal to the second coordinate axis y. The magnet unit 20 surrounds an examination opening 90 for receiving a patient 80. In the present example embodiment, the examination opening 90 is cylindrical and surrounded in a circumferential direction by the magnet unit 20 in a hollow-cylindrical shape. However, in principle an embodiment of the examination opening 90 deviating therefrom is conceivable at any time. The patient 80 can be pushed into the examination opening 90 via a patient support appliance 70. To this end, the patient support appliance 70 comprises a patient table embodied movably within the examination opening 90. The magnet unit 20 comprises a main magnet 21 for the generation of a strong and in particular homogeneous main magnetic field within the examination opening 90. The magnet unit 20 is screened from the outside via a first housing 26.

The magnet unit 20 furthermore comprises a gradient coil unit 22 for the generation of magnetic field gradients, which are used for spatial encoding during imaging. The gradient coil unit 22 is controlled via a gradient control unit 53 of the MR-control and evaluation unit 50. The magnet unit 20 furthermore comprises a radio-frequency antenna unit 23, which, in the present example embodiment, is embodied as a body coil which is permanently integrated in the magnet unit 20. The radio-frequency antenna unit 23 is designed to excite atomic nuclei that become established in the main magnetic field generated by the main magnet 21. The radio-frequency antenna unit 23 is controlled by a radio-frequency antenna control unit 52 of the MR-control and evaluation unit 50 and irradiates radio-frequency alternating fields into an examination chamber, which is substantially formed by an examination opening 90 of the magnet unit 20. The radio-frequency antenna unit 23 is furthermore embodied to receive magnetic-resonance signals.

The gradient coil unit 22 can in particular generate magnetic fields with a gradient in the direction of the first rotated coordinate axis x', in the direction of the second rotated coordinate axis y' or in the direction of the third coordinate axis y. To this end, in this example embodiment, the gradient coil unit 22 comprises three gradient-coil subunits, each of which is able to generate a magnetic field with a gradient in the direction of one of the coordinate axes x', γ', ζ'. In this case, an arrangement is known for each of the three gradient-coil subunits so that each gradient-coil subunit is arranged outside the first region of the magnet unit 20.

To control the main magnet 21, the gradient coil unit 22 and to the control the radio-frequency antenna unit 23, the magnet unit 20 is connected to an MR-control and evaluation unit 50. The MR-control and evaluation unit 50 controls the magnet unit 20 centrally via a system control unit 51, such as, for example, for the performance of a predetermined imaging gradient-echo sequence. In this case, the control is effected via a radio-frequency antenna control unit 52 and a gradient control unit 53. The MR-control and evaluation unit 50 also comprises an evaluation unit, which is not shown in any more detail, for the evaluation of medical image data acquired during the magnetic-resonance examination. In addition, the MR-control and evaluation unit 50 comprises a user interface, which is not shown in any more detail, this comprises a display unit 54 and an input unit 55, each of which are connected to the system control unit 51. Control information such as, for example, imaging parameters, and reconstructed magnetic-resonance images can be displayed on the display unit 54, for example on at least one monitor, for a medical operator. The input unit 55 can be used by the medical operator to input information and/or parameters during a scanning process.

If the magnet unit 20 is embodied to rotate about the examination volume 90, and the gradient coil unit 22 is embodied to rotate simultaneously with the magnet unit 20, the gradient coil pulse sequences are modified such that to ensure that the vectors of the gradient magnetic fields in the plane orthogonal to the third coordinate axis z do not rotate with respect to the patient.

Figure 7:
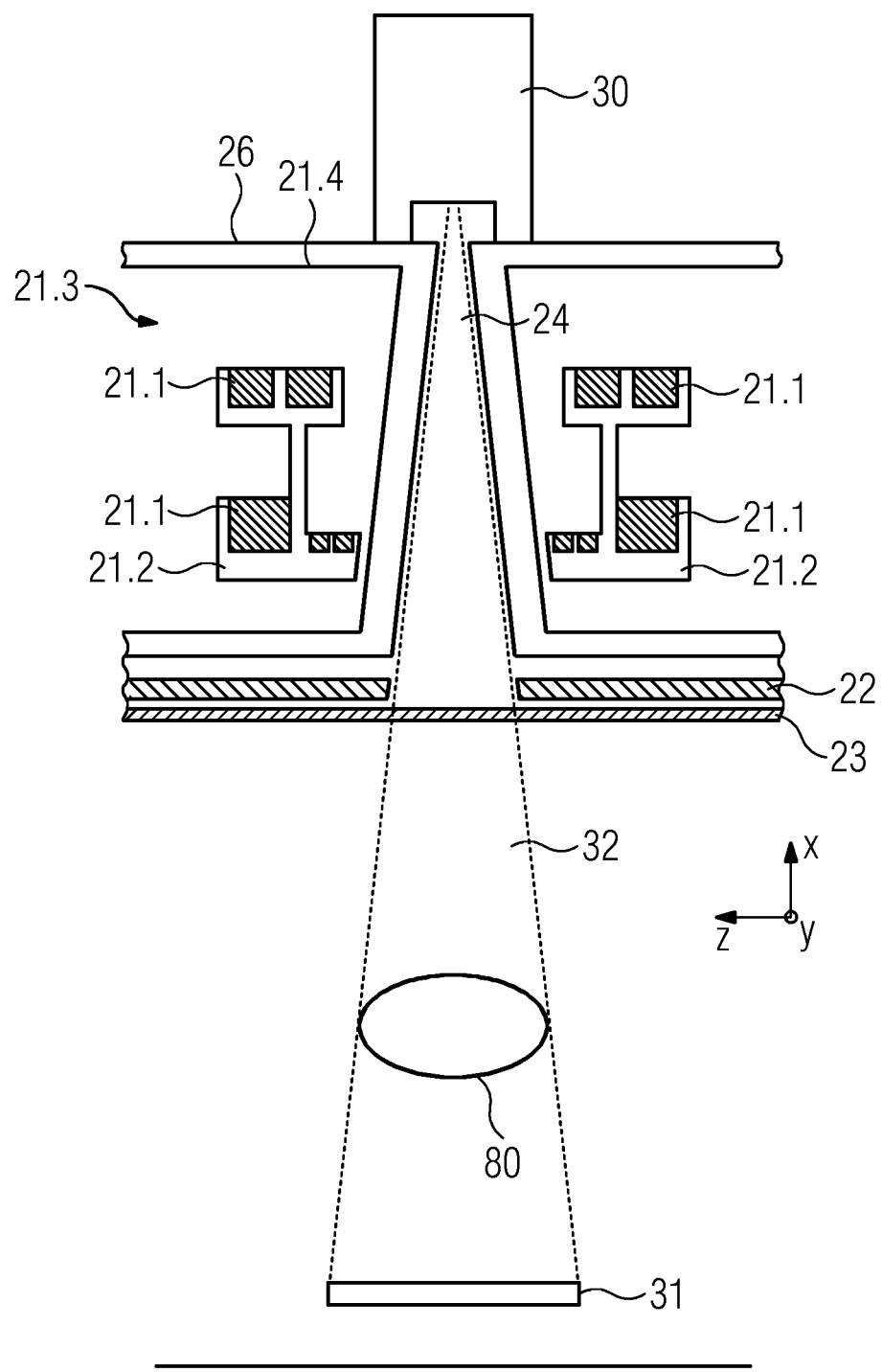
FIG. 7 shows a section through the funnel of a magnet unit.

FIG. 7 shows a section orthogonal to the first rotated coordinate axis y' through a funnel 24 through the magnet unit 20. In the example embodiment shown, the funnel 24 extends through the main magnet 21 and the gradient coil unit 22, but not through the radio-frequency antenna unit 23. In this example embodiment, the radio-frequency antenna unit 23 is at least partially embodied as penetrable to radiation 32 from the first radiation unit 30. It is also possible for the funnel 24 to penetrate the radio-frequency antenna unit 23. It is furthermore possible for the funnel 24 not to penetrate the gradient coil unit 22; in this case the gradient coil unit 22 must be embodied to be at least partially penetrable by radiation 32 from the first radiation unit 30. The funnel 24 penetrates the main magnet 21 such that the main magnet 21, in particular the coil elements 21.1, can generate a homogeneous magnetic field in the examination opening 90. In the example embodiment shown, the main magnet 21 comprises a plurality of superconducting coil elements 21.1 on a coil carrier 21.2, which are surrounded by a coolant 21.3. In this case, the superconducting coil elements 21.1 encircle the examination opening 90. The coil carrier 21.2 on the one hand provides mechanical stability and dimensional stability of the coil elements 21.1 and also cooling of the coil elements 21.1.

If in this embodiment the magnet unit 20 is embodied to rotate about the examination volume 90, and the gradient coil unit 22 is embodied to rotate simultaneously with the magnet unit 20, the gradient coil pulse sequences are modified such that the vectors of the gradient magnetic fields in the plane orthogonal to the third coordinate axis do not rotate with respect to the first coordinate axis x and the second coordinate axis y, but such that they do rotate with respect to the first rotated coordinate axis x' and the second rotated coordinate axis y'.

Figure 8:
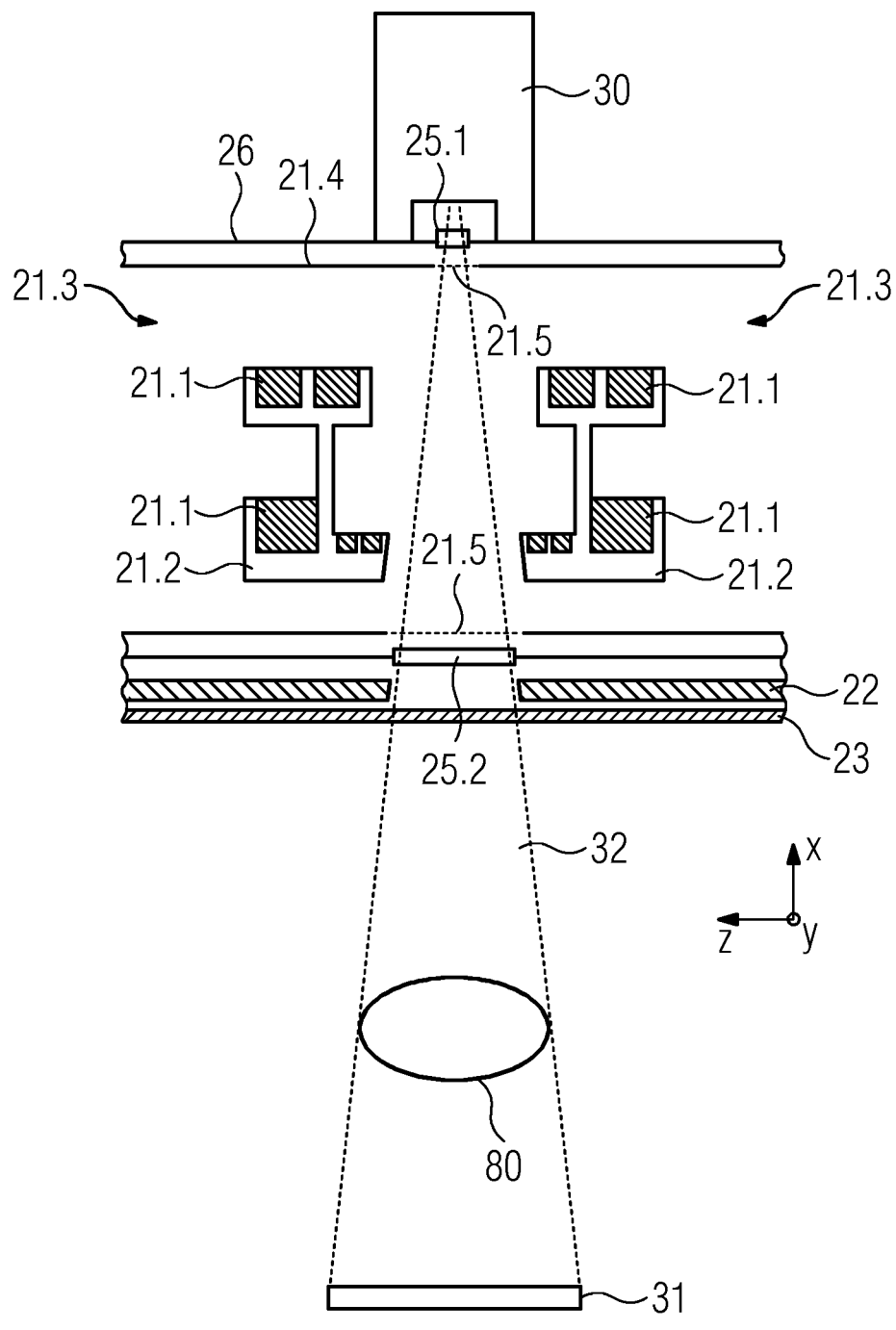
FIG. 8 shows a section through the window of a magnet unit.

FIG. 8 shows a section orthogonal to the first rotated coordinate axis y" through the external window 25.1 and the internal window 25.2 of the magnet unit 20. In the example embodiment shown, the external window 25.1 and the internal window 25.2 are a part of the first housing 26 of the magnet unit 20. Here, both the external window 25.1 and the internal window 25.2 are embodied as rectangular. Obviously, other window shapes are also possible, in particular round windows 25.1, 25.2. In this example embodiment, the thermal insulation 21.4 also comprises regions 21.5 which are penetrable by the radiation 32 from the first radiation unit 30. These regions 21.5 of the thermal insulation 21.4 can, for example, be constructed from the material of the thermal insulation 21.4, but embodied thinner than the first housing 26 outside the region. The regions 21.5 of the thermal insulation 21.4 can also be made of a metal foil, in particular aluminum foil or copper foil.

In the example embodiment shown, the external window 25.1 and the internal window 25.2 are made of beryllium. It is furthermore possible for the windows 25.1, 25.2 to be made of another material that is transparent to the radiation 32 from the first radiation unit 30, for example aluminum or glass.

In the example embodiment shown, the electrically conductive material of the coil elements 21.1 is magnesium diboride MgB2. The critical temperature 39 K of magnesium diboride $MgB_2$ is above the boiling point 4.2 K at normal pressure, 1013 hPa. Alternative electrically conductive materials for the coil elements 21.1 are also conceivable, in particular superconducting materials, and in particular superconducting materials with a critical temperature above the boiling point 4.2 K of helium at normal pressure, 1013 hPa, for example niobium-germanium NbsGe with a critical temperature of 23 K.

In the example embodiment shown in both FIG. 7 and FIG. 8 shown, the cooling takes place by heat conduction via the coil carrier 21.2 in that the coil carrier 21.2 is cooled via a tube system, wherein a coolant for heat transfer is circulated in the tube system and the heat is transferred to a heat exchanger. This can be supported by way of an optional gaseous coolant 21.3. The tube system, which is not shown in FIG. 7, is embodied such that it is not embodied in the first region of the magnet unit 20 in order to improve the transparency of the first region to radiation 32 from the first radiation unit 30. Alternatively, and in particular in the case of magnet units 20 which are embodied not to rotate, the coil elements 21.1 can be cooled by immersion in a coolant 21.3, for example in liquid helium 21.3. A tube system of this kind is, for example, known from DE 10 2004 061 869 B4.

In the example embodiment shown in both FIG. 7 and FIG. 8, the coil elements 21.1 of the main magnet 21 and the coil carrier 21.2 of the main magnet 21 are not arranged in the first region of the magnet unit 20. In addition no parts of the coil elements 21.1 and no parts of the coil carrier 21.2 are arranged in the first region of the magnet unit 20. In the case of a magnet unit 20, the coil elements 21.1 typically encircle the examination axis 91 in a ring shape, in order to generate a homogeneous magnetic field in the direction of the third coordinate axis z when there is a current flow in the examination opening 90. The ring-shaped coil elements 21.1 are spaced apart from one another with respect to the third coordinate axis z. To ensure no parts of the coil elements 21.1 are embodied in the first region of the magnet unit 20, it is in particular possible to select a distance between two different coil elements 21.1 that is greater than the extension of the first region with respect to the third coordinate axis z and the two different coil elements 21.1 can be arranged on different sides of the first region. This distance can in particular be greater than the distances between all the other adjacent coil elements 21.1. In particular, it is also possible to arrange the two different coil elements 21.1 on different sides of the first region, so that the distance between the two coil elements 21.1 with respect to the third coordinate axis z is larger near the first region than far away from the first region.

In the example embodiment shown in FIG. 7 and FIG. 8, the coil carrier 21.2 embodies a continuous opening in the first region which is greater than the extension of the beam path of the radiation 32 through the coil carrier 21.2. Alternatively, it is conceivable to arrange in each case at least one separate coil carrier 21.2 on different sides of the first region. It is furthermore also possible to use a material which is transparent to the radiation 32 from the first radiation unit 30 as the material of the coil carrier 21.2. The coil carrier 21.2 is advantageously made of a material with high thermal conductivity and low mechanical deformability, in particular metal, in particular aluminum. In particular the coil carrier 21.2 can be embodied to cool the coil elements 21.1 of the main magnet 20 by way of heat conduction, in particular the thermal conductivity of the material of the coil carrier 21.2 can be above 10 W/(m-K), in particular above 20 W/(m-K), in particular above 50 W/(m-K), or in particular above 100 W/(m-K). Here the unit W/(m-K) is an abbreviation for Watts per meter and per Kelvin.

Figure 9:
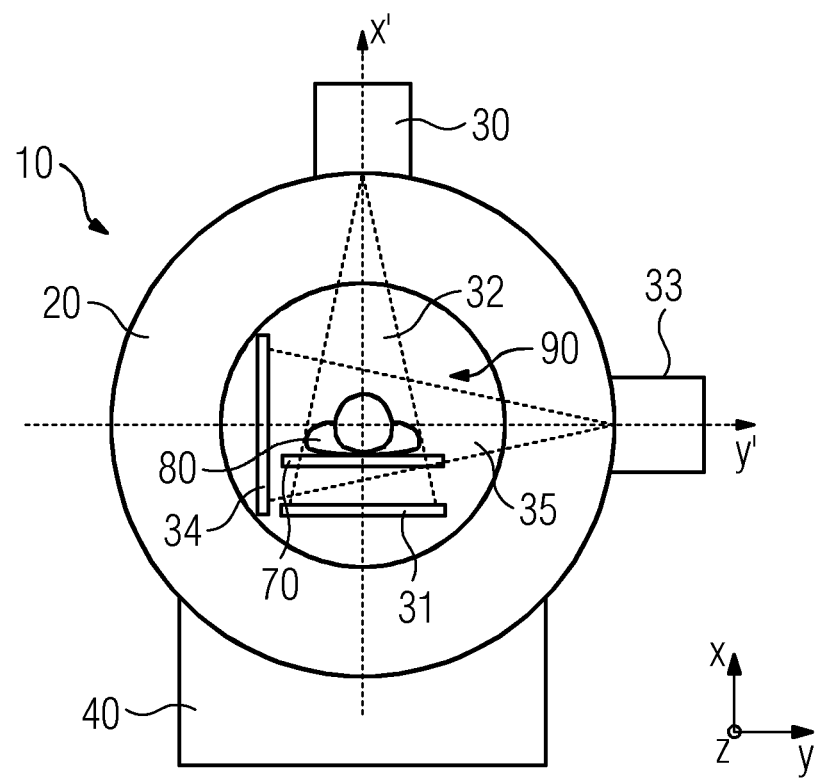
FIG. 9 shows a medical imaging system with a second X-ray source and a second X-ray detector.

FIG. 9 shows a schematic section through a medical imaging system 10 with a first X-ray source 30, a second X-ray source 33, a first X-ray detector 31 and a second X-ray detector 34. In this case, the first X-ray source 30 is embodied to emit X-rays 32 through the magnet unit 20 and through the examination object 80 in the direction of the first rotated coordinate axis x'' to the first X-ray detector 31, the second X-ray source 33 is embodied to emit X-rays 35 through the magnet unit 20 and through the examination object 80 in the direction of the second rotated coordinate axis y' to the second X-ray detector 34. In this case, the rotated coordinate axis x' is orthogonal to the rotated coordinate axis y', and both rotated coordinate axes are orthogonal to the examination axis 91 and hence to the coordinate axis z.

This arrangement enables two X-ray projections to be recorded simultaneously with respect to orthogonal projection directions. The two X-ray projections can be used to reconstruct a three-dimensional image data set. In the example embodiment shown, the magnet unit 20 is embodied to rotate about the examination opening 90, in particular about the examination axis 91. The first X-ray source 30, the first X-ray detector 31, the second X-ray source 33 and the second X-ray detector 34 are embodied to rotate simultaneously with the magnet unit 20 about the examination opening 90, in particular about the examination axis 91, for example in that they are permanently connected to the magnet unit 20.

In FIG. 9, the connecting line between the first X-ray source 30 and the first X-ray detector 31 corresponds to the coordinate axis x' and the connecting line between the second X-ray source 33 and the second X-ray detector 34 corresponds to the coordinate axis y'. In this example embodiment, the connecting lines are orthogonal to one another, but other angles are also possible.

Figure 10:
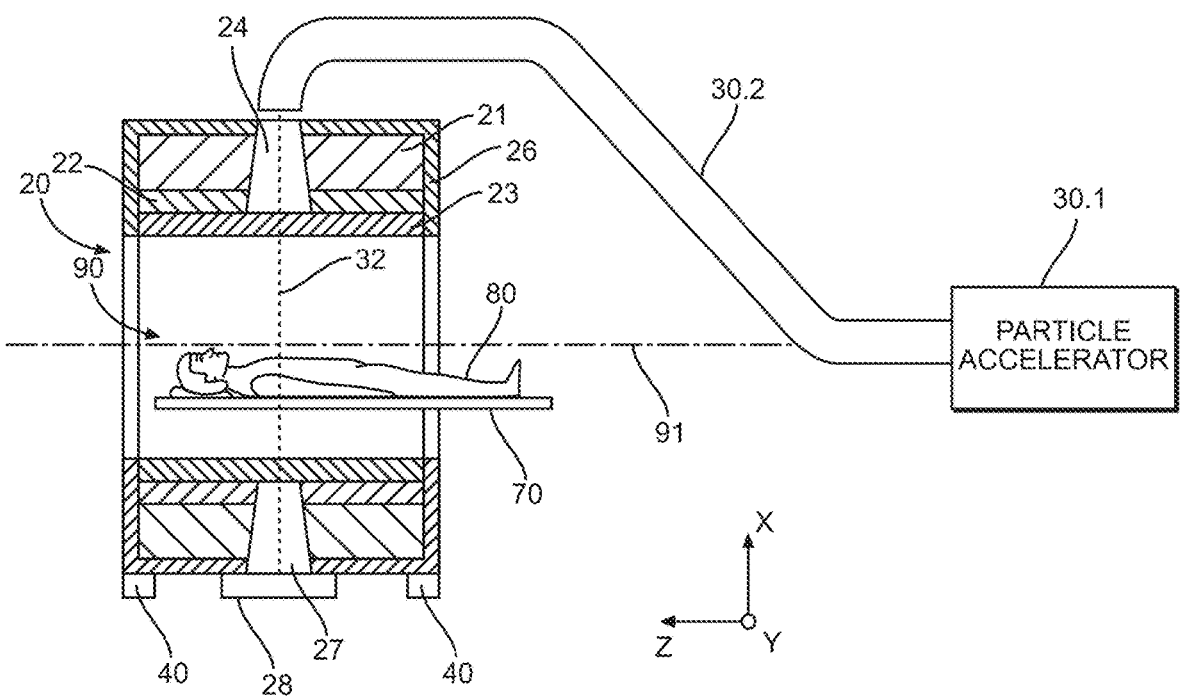
FIG. 10 shows a medical imaging system with a first particle radiation unit comprising a particle accelerator and a particle-beam guide.

FIG. 10 shows a schematic section through a medical imaging system 10 orthogonal to the second coordinate axis y. In addition to the magnet unit 20, the medical imaging system 10 comprises a radiation unit 30 with a particle accelerator 30.1 and a mobile particle-beam guide 30.2 for charged particles (an English technical term for a mobile particle-beam guide is "gantry"). In this example embodiment, the particle accelerator 30.1 is embodied as stationary and the particle-beam guide 30.2 is embodied to rotate about the examination opening 90, in particular about the examination axis 91. In the example embodiment shown, the magnet unit 20 is furthermore embodied to rotate about the examination opening 90. In this case, the particle-beam guide 30.2 and the magnet unit 20 are embodied for simultaneous rotation. The mobile particle-beam guide 30.2 comprises deflecting units that generate a magnetic field and guides the particles on curves along the particle-beam guide 30.2 by way of the Lorentz force acting on charged particles. In this case, the strength of the magnetic fields of the particle-beam guide 30.2 can be adapted for the mass, the charge and the speed of the guided particles.

In this example embodiment, the medical imaging system 10 furthermore comprises an outlet region 27 and a screen 28. The outlet region 27 is embodied such that the radiation 32 sent by the radiation unit 30 through the funnel 24 to the examination object 80 leaves the magnet unit 20 through the outlet region 27. This ensures that the particle radiation 32 does not damage the magnet unit 20. The screen 28, which is advantageously made of lead, absorbs the particle beam 32 to prevent the particle radiation 32 posing a hazard.

In the example embodiment shown, the outlet region 27 of the magnet unit 20 is arranged with respect to the examination axis 91 directly opposite the funnel 24 of the magnet unit 20. It is however also possible to embody the outlet region 27 at another position so that the deflection of the radiation 32 by the main magnetic field of the main magnet 21 is taken into account.

Figure 11:
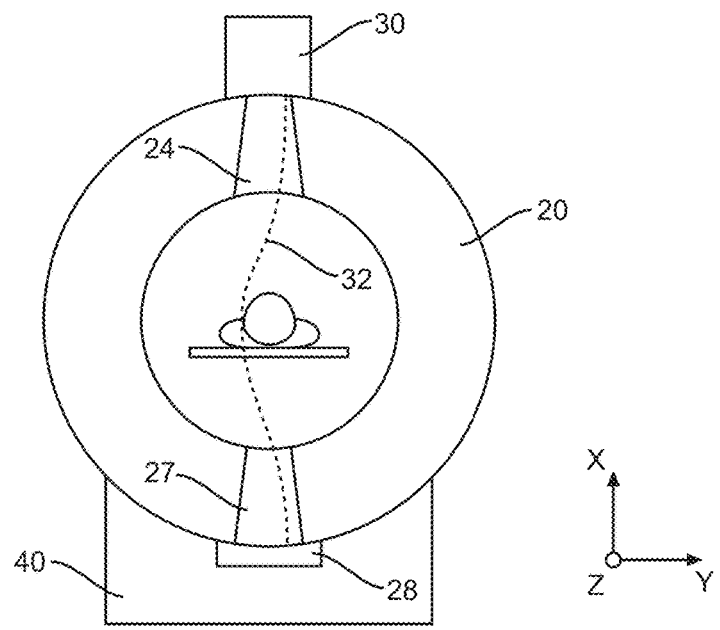
FIG. 11 shows a medical imaging system with a particle radiation unit, wherein the particle radiation unit emits electrically charged particle radiation.

FIG. 11 shows a further section of the medical imaging system 10 shown in FIG. 10. Since the main magnet 21, the gradient coil unit 22 and the radio-frequency antenna unit 23 generate time-constant or time-variant magnetic or electrical fields, radiation 32 consisting of electrically charged particles is diverted by the Lorentz force. In this example, the first radiation unit 30 is embodied to adapt the speed and the direction of the electrically charged particles in the particle beam 32 such that they arrive at a predefined part of the examination object 80 taking account of the electrical and magnetic fields prevailing in the examination opening 90.

In order to match the particle radiation unit 30 with the magnetic field of the magnet unit 20, in this example embodiment, the radiation-control and evaluation unit 60 and the MR-control and evaluation unit 50 are connected, in this case the MR-control and evaluation unit 50 provides information on the magnetic field in the magnet unit 20 to the radiation-control and evaluation unit 60, which adapts the speed and the direction of the particles of the particle radiation 32. It is, however, also possible to embody the radiation-control and evaluation unit 60 and the MR-control and evaluation unit 50 as a common control and evaluation unit, which controls both the magnet unit 20 and the first radiation unit 30 and evaluates the data obtained.

In the example embodiment shown, the MR-control and evaluation unit 50 furthermore transmits MR image data sets to the radiation-control and evaluation unit 60. The radiation-control and evaluation unit 60 can then control the radiation unit 30 such that the radiation 32 arrives at a predetermined part of the examination object 80. In this case, a possible movement of the predetermined part of the examination object 80 due to changes or movements of the examination object 80 can be detected by an analysis of the MR image data sets and compensated via the radiation-control and evaluation unit 60.

Figure 12:
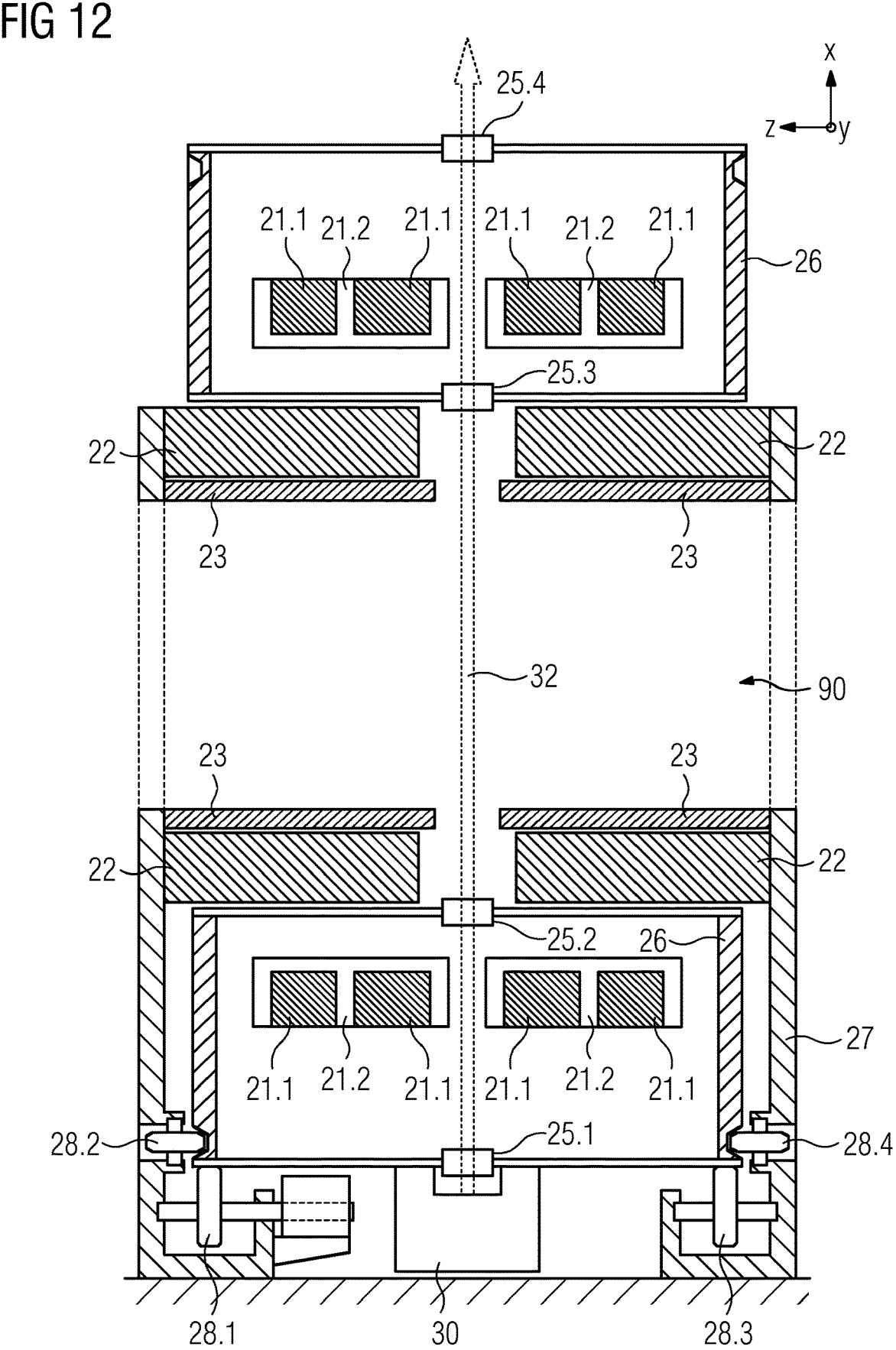
FIG. 12 shows a section through the medical imaging system, where the main magnet can be rotated independently from the gradient coil unit and the radio-frequency antenna.
Figure 13:
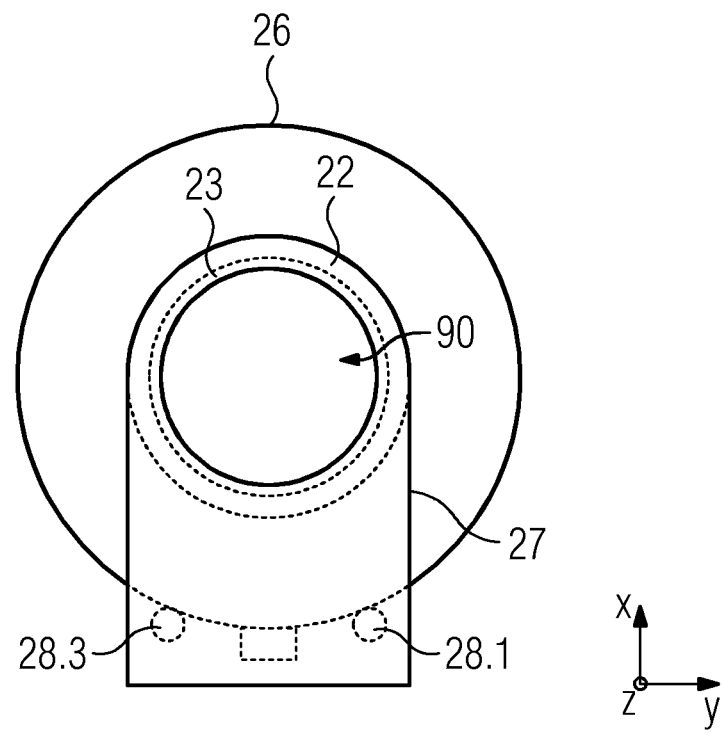
FIG. 13 shows a lateral view of the medical imaging system, where the main magnet can be rotated independently from the gradient coil and the radio-frequency antenna.

FIG. 12 shows a section through the medical imaging system, where the main magnet 21 can be rotated independently from the gradient coil unit 22 and the radio-frequency antenna 23. FIG. 13 shows a lateral view of the same embodiment of the medical imaging system. In this embodiment, the main magnet 21 comprises several coil elements 21.1 and coil carriers 21.2 within a first housing 26. The main magnet is embodied to rotate simultaneously with the first housing 26 about the examination axis 91. The first housing 26 comprises further means for cooling the several coil elements 21.1, which are not displayed due to clearness. In this embodiment, the first radiation unit 30 is a radioactive Cobalt-60 source, which is embodied to emit gamma radiation, and which is embodied to rotate simultaneously with the main magnet 21 by being attached to the second housing 27 of the main magnet 21. Since the radioactive Cobalt-60 within the radioactive Cobalt-60 source cannot be controlled to stop emitting gamma radiation, the radioactive Cobalt-60 source comprises a closable shutter for blocking the gamma radiation 32, whenever no gamma radiation 32 is needed in the examination volume. Alternatively, the first radiation unit 30 can also be a X-ray source, another gamma radiation source or a particle radiation source.

The gradient coil unit 22 and the radio-frequency antenna 23 are attached to a second housing 27. The second housing 27 as well as the gradient coil unit 22 and the radio-frequency antenna 23 are fixed and are not embodied to rotate about the examination axis.

In this embodiment the second housing 27 is not a closed housing, but is embodied to support the gradient coil unit 22 and the radio-frequency antenna 23 only from one side. In particular the second housing 27 is embodied to not interfere with the radiation 32 of the first radiation source 30. Furthermore, the gradient coil unit 22 and the radio-frequency antenna 23 are split, in other words there two cylindrical gradient coils subunits 22.1, 22.2 that form the gradient coil unit 22, and there are two cylindrical radio-frequency sub-antennas 23.1, 23.2 that form the radio-frequency antenna 23. If the radiation 32 has the coordinate value 0 with respect to the third coordinate axis z, then the first gradient coil subunit 22.1 has positive coordinates with respect to the third coordinate axis z, and the second gradient coil subunit 22.2 has negative coordinates with respect to the third coordinate axis z, furthermore, the first radio-frequency subantenna 23.1 has positive coordinates with respect to the third coordinate axis z, and the second radio-frequency subantenna 23.2 has negative coordinates with respect to the third coordinate axis z. Alternatively, the second housing 27 is a closed housing. In this alternative embodiment, the second housing 27 is embodied to be transparent for the radiation 32 of the first radiation source 30 in the same way as the different embodiments of the first housing 26 are embodied to be transparent for the radiation 32 of the first radiation source, for example by comprising an external window and an internal window or by embodying a funnel.

Furthermore, in this embodiment the medical imaging system 10 comprises means 28.1, 28.4 for rotating the first housing 26 within the second housing 27. In this embodiment the means 28.1, 28.4 are rubber wheels, where one rubber wheel 28.1 is driven by an engine, and where the other rubber wheels 28.2, 28.3, 28.3 guide the rotation of the first housing 26 within the second housing 27. Alternatively it is also possible to drive more than one of the means 28.1, 28.4 for rotating the first housing 26.

In this embodiment the magnet unit 20 comprises an internal window 25.2 and an external window 25.1 in the first housing 26 within the first region, where both the internal window 25.2 and the external window 25.1 are transparent for the radiation 32. The internal window 25.2 and the external window 25.1 can in particular be made of beryllium; alternatively they can be made of another material like aluminum or glass. Alternatively the first region can also be embodied as a funnel 24 in the magnet unit 20 extending radially to the examination axis 91, and wherein the first region is transparent to the radiation 32 emitted by the first radiation unit 30 radially to the examination axis 91.

In this embodiment there is only one first radiation unit 30 attached to the magnet unit 20, where the first radiation unit 30 is embodied as a Cobalt-60 source, furthermore, the magnet unit comprises only one first region that is transparent to radiation 32 emitted by the first radiation unit 30. Alternatively and additionally, there can be a second radiation unit 33 attached to the magnet unit 20, the magnet unit comprises can comprise a second region that is transparent to radiation 35 emitted by the second radiation unit 33.

The invention claimed is:

1. A medical imaging system, comprising:
a magnet unit configured for magnetic resonance imaging of an examination object, the magnet unit including a main magnet and a first housing, the main magnet being arranged inside the first housing and the main magnet including coil elements and at least one coil carrier, the magnet unit defining an examination opening along an examination axis such that the magnet unit surrounds the examination opening; and
a first radiation unit configured to irradiate the examination object and arranged on a surface of the magnet unit facing away from the examination opening,
wherein the magnet unit includes a first region, the first region being transparent to radiation emitted by the first radiation unit radially to the examination axis,
the first radiation unit is configured to emit the radiation through the first region of the magnet unit in a direction of the examination opening and the first radiation unit is furthermore embodied to rotate about the examination axis, and
the first region of the magnet unit includes at least one internal window in the first housing and at least one external window in the first housing, the at least one internal window and the at least one external window are transparent to the radiation emitted by the first radiation unit, a material of the at least one internal window and a material of the at least one external window being more transparent than a material of the first housing, wherein
the first radiation unit is a first X-ray source,
the medical imaging system furthermore includes a first X-ray detector, and
the first X-ray source and the first X-ray detector are configured for X-ray imaging of the examination object,
wherein the main magnet, the first X-ray source, and the first X-ray detector are connected such that the main magnet, the first X-ray source, and the first X-ray detector are configured to rotate together simultaneously about the examination axis.

2. The medical imaging system of claim 1, wherein the coil elements and the at least one coil carrier of the main magnet, are arranged outside the first region of the magnet unit.

3. The medical imaging system of claim 2, wherein the first region is a funnel in the magnet unit, extending radially to the examination axis, and wherein the first region is transparent to the radiation emitted by the first radiation unit, radially to the examination axis.

4. The medical imaging system of claim 2,
wherein the first X-ray detector is arranged on a side of the examination object facing away from the first X-ray source.

5. The medical imaging system of claim 1, wherein the first region is a funnel in the magnet unit, extending radially to the examination axis, and wherein the first region is transparent to the radiation emitted by the first radiation unit, radially to the examination axis.

6. The medical imaging system of claim 1,
wherein the first X-ray detector is arranged on an opposite side of the examination object than the first X-ray source.

7. The medical imaging system of claim 6, further comprising:
a second radiation unit, the magnet unit including a second region that is transparent to radiation emitted by the second radiation unit, radially to the examination axis, the second radiation unit being arranged on the side of the magnet unit facing away from the examination opening,
the second radiation unit being configured to emit radiation through the second region of the magnet unit in the direction of the examination opening, and
the second radiation unit being configured to rotate about the examination opening.

8. The medical imaging system of claim 7, further comprising:
a second X-ray detector,
wherein the second radiation unit is a second X-ray source,
wherein the second X-ray detector is arranged on a side of the examination object facing away from the second X-ray source, and
wherein the second X-ray source and the second X-ray detector are configured for X-ray imaging of the examination object.

9. The medical imaging system of claim 8, wherein a connecting line runs from the first X-ray source to the first X-ray detector, and another connecting line runs from the second X-ray source and second X-ray detector, the connecting line and the another connecting line enclosing an angle of between 60 and 120 degrees.

10. The medical imaging system of claim 9, wherein the connecting line and the another connecting line enclose an angle of between 80 and 100 degrees.

11. The medical imaging system of claim 10, wherein the connecting line and the another connecting line enclose an angle of between 85 and 95 degrees.

12. The medical imaging system of claim 8, wherein the second X-ray source and the second X-ray detector are connected to the main magnet, the first X-ray source, and the first X-ray detector such that the second X-ray source, the second X-ray detector, the main magnet, the first X-ray source, and the first X-ray detector are configured to rotate together simultaneously about the examination axis.

13. The medical imaging system of claim 1, wherein the magnet unit is configured to rotate about the examination opening.

14. The medical imaging system of claim 1, wherein the magnet unit comprises a gradient coil unit, wherein an orientation of the gradient coil unit is fixed relative to the examination opening, and wherein the main magnet is configured to rotate about the examination opening.

15. The medical imaging system of claim 1, wherein the magnet unit is designed to cool the coil elements of the main magnet via heat conduction.

16. The medical imaging system of claim 15, wherein waste heat from the coil elements of the main magnet is dissipated by pipes containing a circulating coolant.

17. The medical imaging system of claim 1, wherein the coil elements of the main magnet are made of an electrically superconducting material, and wherein a critical temperature of the electrically superconducting material is higher than a boiling point of helium.

18. The medical imaging system of claim 1, wherein at least one of the at least one internal window or the at least one external window include beryllium.

19. The medical imaging system of claim 18, wherein the at least one internal window and the at least one external window include beryllium.

\* \* \* \* \*